US006775623B2

United States Patent
Ali et al.

(10) Patent No.: US 6,775,623 B2
(45) Date of Patent: Aug. 10, 2004

(54) REAL-TIME NITROGEN OXIDES (NOX) ESTIMATION PROCESS

(75) Inventors: Moataz Ali, Madison, WI (US); Anupam Gangopadhyay, Troy, MI (US)

(73) Assignee: General Motors Corporation, Detroit, MI (US)

( * ) Notice: Subject to any disclaimer, the term of this patent is extended or adjusted under 35 U.S.C. 154(b) by 119 days.

(21) Appl. No.: 10/269,846

(22) Filed: Oct. 11, 2002

(65) Prior Publication Data

US 2004/0073381 A1 Apr. 15, 2004

(51) Int. Cl.[7] ............................................. G01N 31/00
(52) U.S. Cl. ..................... 702/31; 702/24; 73/23.31; 60/276; 60/274; 60/285; 123/435; 123/677; 123/678
(58) Field of Search ...................... 702/31, 24; 73/23.31; 60/276, 274, 285; 123/435, 677, 678

(56) References Cited

U.S. PATENT DOCUMENTS

| | | | |
|---|---|---|---|
| 4,381,748 A | * | 5/1983 | Eckert et al. ............ 123/406.28 |
| 5,219,227 A | * | 6/1993 | Yang et al. ................. 374/143 |
| 5,431,042 A | | 7/1995 | Lambert et al. .............. 73/116 |
| 6,422,219 B1 | | 7/2002 | Savonen et al. ......... 123/568.12 |
| 6,557,528 B2 | * | 5/2003 | Hiltner .................. 123/406.42 |
| 6,697,729 B2 | * | 2/2004 | Wright ...................... 701/104 |
| 2004/0050362 A1 | * | 3/2004 | Daudel et al. .............. 123/435 |

FOREIGN PATENT DOCUMENTS

GB  2381872 A  *  5/2003  ........... F02D/35/00

OTHER PUBLICATIONS

J. Keck, "Rate–controlled constrained–equilibrium theory of chemical reactions in complex systems", Progress in Energy and Combustion Schience, 1990, vol. 2.
Watson, N., Piley A. D., and Marzouk, M., "A Combustion Correlation for Diesel Engine Simulation", SAE 800028, 1980.
M. Ali, J. Kasab, J. moskwa, D. Foster, T. Root, "A modular Diesel Engine System Model Including EGR, VGT, Feedgas Emissions and Aftertreatment", 2000 ASME ICE Fall Technical Meeting, Sep. 2000.

* cited by examiner

Primary Examiner—John Barlow
Assistant Examiner—Anthony T. Dougherty
(74) Attorney, Agent, or Firm—Kathryn A. Marra (57) ABSTRACT

A process for providing a real-time estimation of in-cylinder NOx production rates during a combustion process in an internal combustion engine. The process employs a model that takes into account fundamental in-cylinder variables such as temperature, pressure and oxygen content. The process can be used with calibrated or uncalibrated internal combustion engines and can be used to capture the effects in variations of engine speed, engine torque, EGR, injection timing, and engine boost levels.

12 Claims, 9 Drawing Sheets

REAL-TIME NITROGEN OXIDES (NOX) ESTIMATION PROCESS

BACKGROUND

This disclosure relates generally to diesel engines and more particularly, to systems and methods for real-time estimation of NOx in exhaust gases generated by the diesel engine.

Current production diesel engines generally do not employ any type of NOx estimation system. By omitting any meaningful real-time NOx estimation, it is possible that the diesel engine will perform sub-optimally due to the fact that other engine operational parameters cannot be dynamically adjusted due to potentially changing NOx levels that occur during the combustion process.

Current production methods of estimating NOx, if employed, are generally based upon a lookup table that can only be generated for a fully calibrated engine, i.e., once the exhaust gas recirculation (EGR), boost, fuel quantity, and timing controllers are designed. When using such techniques, real-time control of NOx is not possible because to control NOx, some of the actuators mentioned above are to be changed, thus changing the original values contained in the look up table. Moreover, the use of lookup table methods primarily involves steady state estimation of NOx. Thus, real-time estimation is not provided by these methods and the use of these methods provides an inherent source of error.

BRIEF SUMMARY

Disclosed herein is a process for providing a real-time estimation of in-cylinder NOx production rates during a combustion process in an internal combustion engine. The process comprises receiving a plurality of input values from a combustion chamber of a cylinder, wherein the input values consist essentially of a mass amount of trapped air in the combustion chamber, a mass amount of trapped fuel in the combustion chamber, a total mass of species generated within a combustion zone as a fraction of total in-cylinder mass, and a correlation value from a lookup table derived from an average NOx temperature of a combustion zone in the combustion chamber; and calculating an output signal from the plurality of input values, wherein the output signal produces a real-time estimate of the NOx production rate from the cylinder.

In accordance with another embodiment, a process for providing a real-time estimation of in-cylinder NOx production rates during a combustion process in an internal combustion engine comprises calculating an average temperature value in a combustion zone of a cylinder combustion chamber; correlating the average temperature value to a correlation value in a look-up table; and estimating the in-cylinder NOx production rate from a calculation including the correlation value, an amount of trapped air in the combustion chamber, an amount of trapped unburned fuel in the combustion chamber, and a total mass of species generated within a combustion zone as a fraction of total in-cylinder mass.

The above described and other features are exemplified by the following figures and detailed description.

BRIEF DESCRIPTION OF THE DRAWINGS

Referring now to the figures, which are exemplary embodiments and wherein the like elements are numbered alike.

DETAILED DESCRIPTION

Disclosed herein is a process for providing real-time estimation of nitrogen oxide (NOx) production rates during a combustion process for an internal combustion engine having a plurality of cylinders, each fed by a fuel injector. As used herein the term "real-time" is defined as an instantaneous estimation of the amount of NOx currently being generated at that instance of time within each cylinder. The process for providing real-time NOx estimation employs a model that takes into account fundamental in-cylinder variables such as temperature, pressure, oxygen content, and other like variables. Applying the in-cylinder model provides a robust method for NOx estimation that is suitably applicable and accurate for an entire range of operating speeds and loads together with all possible exhaust gas recirculation (EGR) rates, boost pressures ranging from no boost to the maximum boosting possible (below over-boosting), and timing variations, while simultaneously maintaining stable operation without misfire or excessive hydrocarbon emission. Moreover, the simplicity of the in-cylinder model minimizes computational overhead on the power train control module and can be used to eliminate the use of an expensive engine out NOx sensor.

To define the in-cylinder model, engine combustion and emissions data were analyzed to identify the in-cylinder parameters having the greatest effect on NOx emissions formations. Parameters were then identified on a combustion cycle level, which allows the process to predict the transient behavior and emissions cycle-to-cycle variations. Advantageously, the in-cylinder model can be easily integrated with combustion models.

Figure 1:
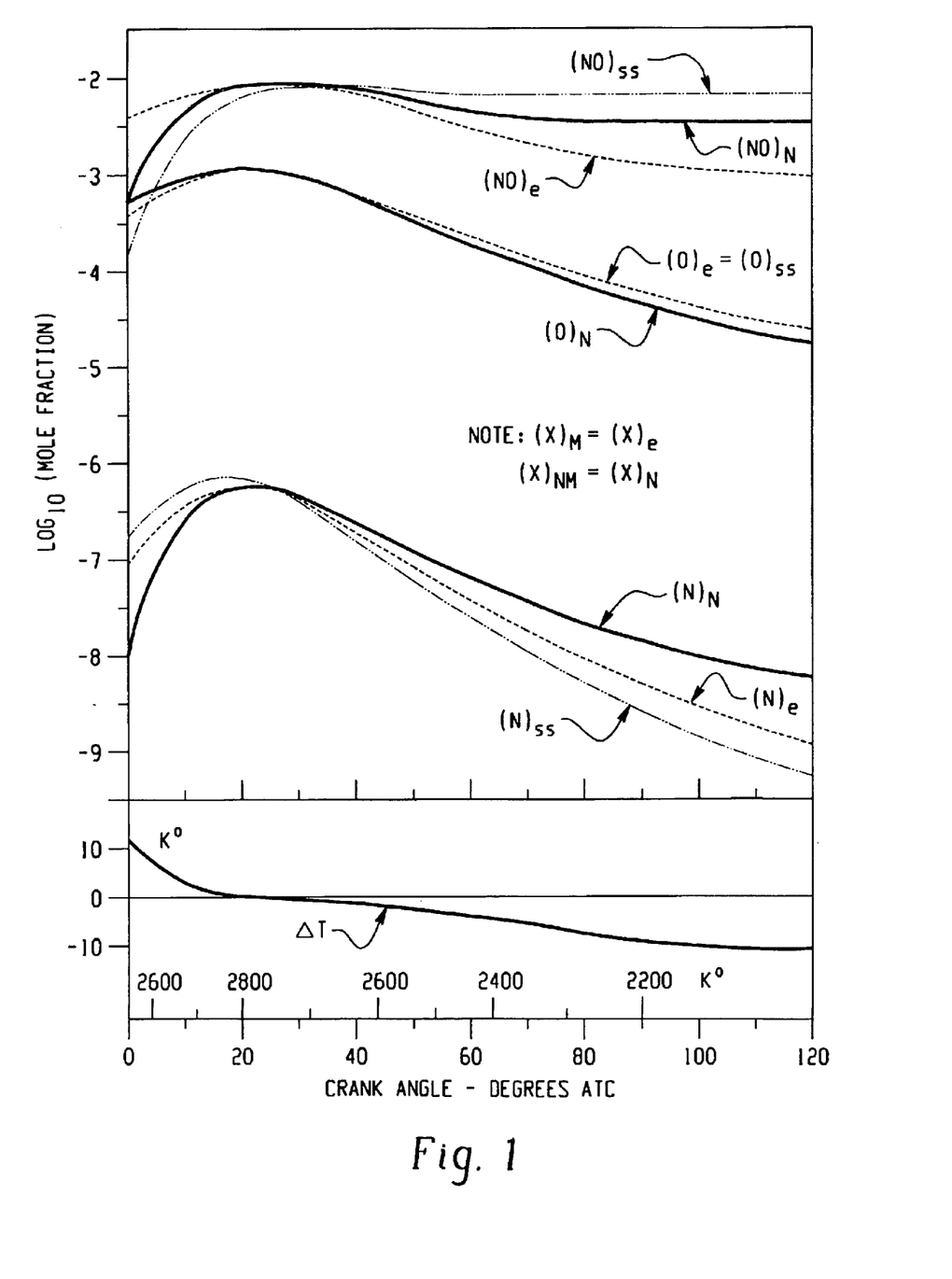
FIG. 1 is a graphical illustration showing steady state and equilibrium calculations for NOx mole fractions as a function of crank angle degrees.

In order to develop the real-time emissions estimation system, some assumptions and simplifications to the emissions formation process were made. For example, as shown in FIG. 1, a comparison of the NOx mole fraction formation history to the equilibrium NOx throughout the combustion and expansion periods showed that the equilibrium concentrations were lower than the steady state values after a peak temperature point. This observation is believed to be attributable to the nature of the chemical kinetics for the NOx reactions. However, it was also observed that during the expansion stroke, the NOx concentration did not change significantly from the peak temperature formation because the temperature drop was much faster than the chemical reactions. This leads to a so called "frozen" NOx concentration, which frozen NOx concentration is about constant at about 90% of the maximum formed at the peak temperature.

Figure 2:
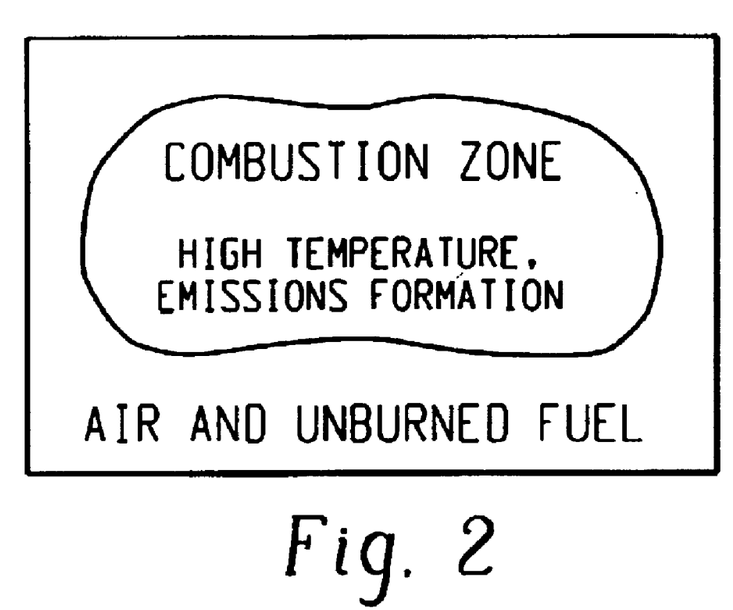
FIG. 2 is a pictorial illustration of combustion zone and an excess air zone with unburned fuel in a combustion chamber cylinder at peak in-cylinder average temperature conditions.

Another assumption and simplification to the emissions formation process is shown in FIG. 2. As shown, each cylinder has been divided into two zones: a combustion zone and an excess air zone. The excess air zone is defined as the region of the cylinder with unburned fuel and air. The combustion zone is defined by the presence of the chemical reactions and formation of NOx species as well as other emissions. The combustion zone can be characterized by having the burned fuel at peak temperature reacting with a stoichiometric amount of air, which also includes an excess amount of nitrogen due to the re-circulated exhaust (i.e., EGR). As such, the oxygen percentage in the exhaust is less than the oxygen in the fresh air. At peak temperature conditions, it is observed that there is an agreement between the equilibrium NOx formations with the steady state measurements. Therefore, the chemical equilibrium calculations can be performed for the combustion zone at the time of peak in-cylinder average temperature conditions to provide an estimate of the amount of NOx produced. The calculations are done at the combustion zone average temperature, not the overall in-cylinder temperature. The chemical equilibrium calculations include minimizing the total Gibbs free energy for all of the species produced in the mixture so as to determine the mole fractions of each component. The term "species" refers to all gaseous components formed in the mixture (combustion zone) including, but not limited to, the nitrogen oxides. Based upon this observation, a look up table can be made based on the chemical equilibrium calculations that correlate to the average temperature condition for the nitrogen oxides produced during both expansion and combustion.

The combustion zone is a non-uniform temperature distribution area, which can result in non-uniform emissions formation. In the present model, it is assumed that the average temperature of the combustion zone is the average NOx producing temperature. However, in most cases, this average NOx producing temperature is different from the actual average temperature due to the non-linear behavior of emissions production as a function of temperature.

The final correlation of the average NOx producing temperature was determined in a simplified form that can be easily implemented, yet can be accurate enough to capture the various effects. The estimation model is dependant on the trapped air mass, the cylinder pressure at maximum temperature, and the cylinder pressure at top dead center. Using these input variables, the in-cylinder model output provides a real-time estimate of the NOx flow rate from the cylinder. This model runs only once per cycle after the maximum temperature has occurred, which provides a significant advantage over chemical reaction integration models in real-time implementation.

The in-cylinder correlation model for providing real-time NOx estimation during combustion cycles can be determined from the following mathematical relationship as represented by formula (I).

$$T_{burn} = a\left(1 + \frac{m_{air}}{m_{stp}}\right)^b \left[1 + \frac{p_{T\,max}}{p_{TDC}}\right]^c, \quad (I)$$

wherein $m_{air}$ is the trapped air mass (expressed in kilograms), $m_{stp}$ is the trapped mass at standard temperature and pressure with a volumetric efficiency of 1 (expressed in kilograms), $P_{Tmax}$ is the cylinder pressure at maximum temperature (expressed in kilopascals), $P_{TDC}$ is cylinder pressure at top dead center (expressed in kilopascals), and a (expressed in degrees Kelvin), b, and c are constants. It should be noted that $T_{burn}$ represents the average NOx producing temperature in the combustion zone as previously described and shown in FIG. 2 rather than a bulk temperature of the burning gas. In operation, the $T_{burn}$ value is then correlated to a look-up table that includes static values based on the chemical equilibrium calculations. Since the look-up table is based on chemical equilibrium calculations and as such, the values contained within the table are static. The values in the look-up table do not change and are independent of actuator changes, engine types, and does not require a steady state estimation of NOx. It is further noted that constants a, b, and c did not show a significant change when increasing the number of test points used for identification.

The model provides exceptional accuracy with the added capability of capturing the different effects that can cause changes in NOx production rates. Although the in-cylinder mathematical model shown in Formula (I) is preferred, a two-dimensional look up table can also be employed to provide similar results. The two-dimensional look-up table could use the mass ratios and pressure ratios as the input values for providing the correlation. Validation of the model was conducted using a 1.3 liter diesel engine with the following inputs recorded as shown in Table 1. The NOx flow rate was estimated under a variety of conditions using the in-cylinder model and compared to actual measurements taken under the same conditions. Engine speed was varied to 1500, 1800, 2400, 2800 and 3000 revolutions per minute (RPM); loads (BMEP) were varied to 0, 200, 400, 600, and 800 kilopascals (kPa); EGR valve duty was varied to 0, 30 and 60 percent. Injection timing was varied at timed (calibrated), +5 degrees, and −5 degrees.

TABLE 1

| CONTROLLING | RECORDED VARIABLES |
| --- | --- |
| RPM (engine speed) | Torque (engine torque) |
| BMEP (brake mean effective speed) | IMEPs (individual cylinders mean effective pressures) |
| EGR DTY (EGR valve duty cycle) | MAIR (air flow rate) |
| SOI (start of injection angle) | MAP (intake manifold absolute pressure) |
| | IMT (intake manifold temperature |
| | CO2_in CO2_out |
| | (intake and exhaust manifold carbon dioxide concentration) |
| | NOx_eng (exhaust NOx concentration (parts per million)) |
| | O2_eng |
| | (exhaust oxygen concentration) |
| | A/F bench |
| | (emissions bench air to fuel ratio) |
| | SOI_pilot (pilot start of injection angle) |
| | fuel_main (main fuel injection desired volumetric flow rate) |
| | fuel_pilot (pilot fuel injection desired volumetric flow rate) |
| | smoke (Bosch smoke number) |

TABLE 1-continued

| CONTROLLING | RECORDED VARIABLES |
|---|---|
| | EGR % (percentage of EGR to fresh air) |

Figure 3:
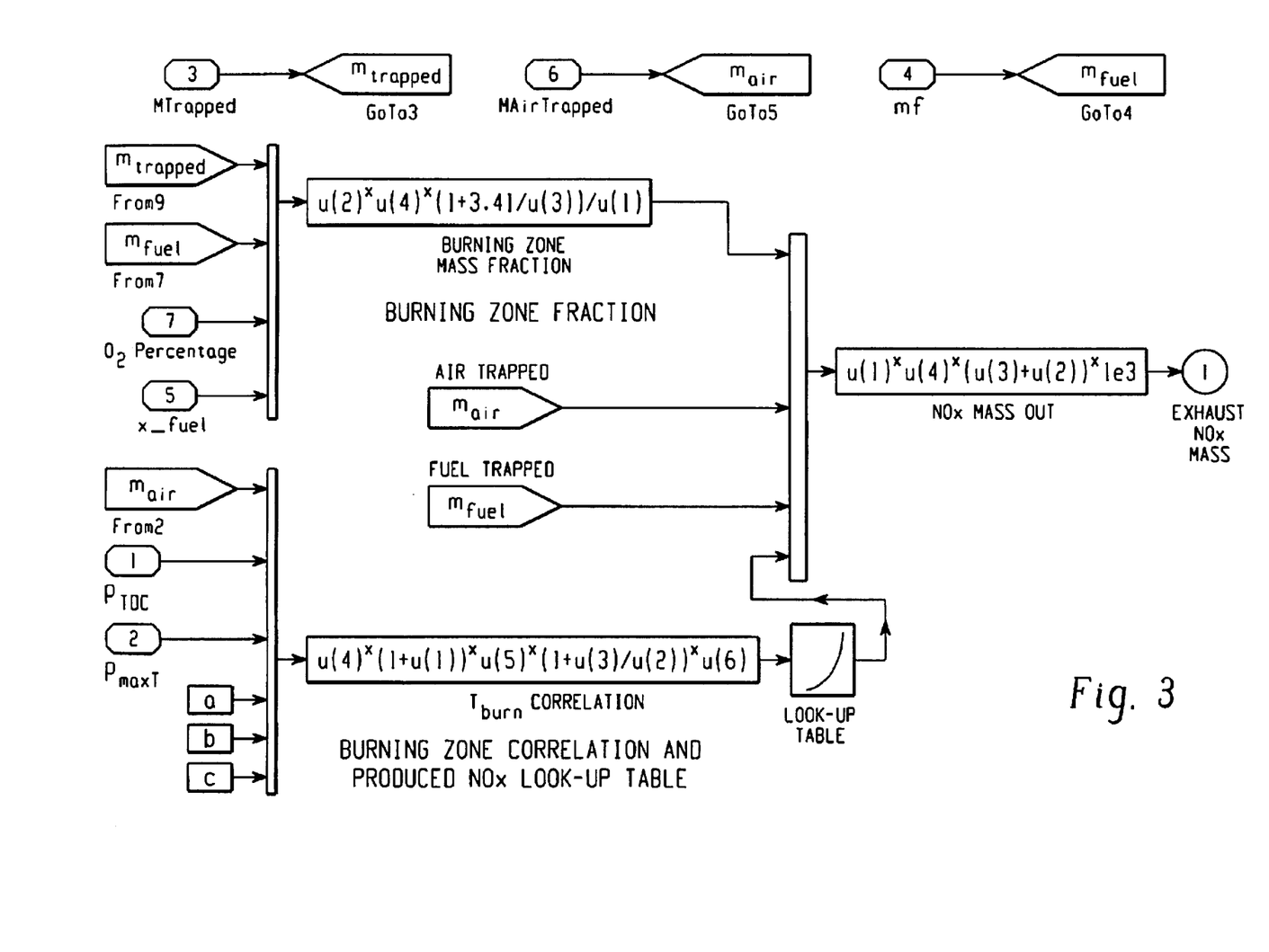
FIG. 3 is a block diagram of a NOx estimation model in a Matlab/Simulink format.
Figure 4:
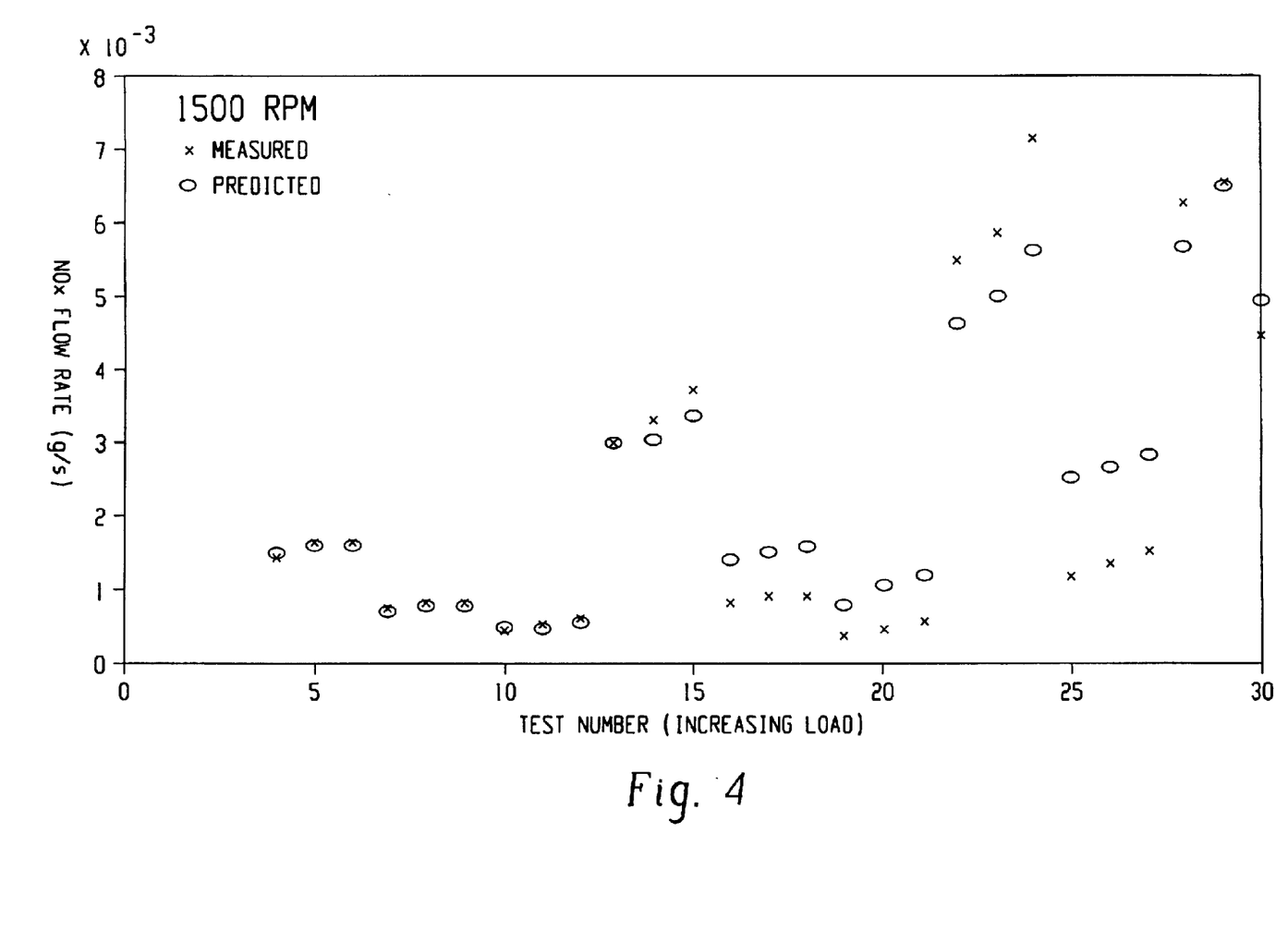
FIG. 4 is a graphical illustration of model predictions and measurement of NOx flow rate as a function of test number for a 1.3 liter engine running at 1,500 revolutions per minute (rpm)
Figure 5:
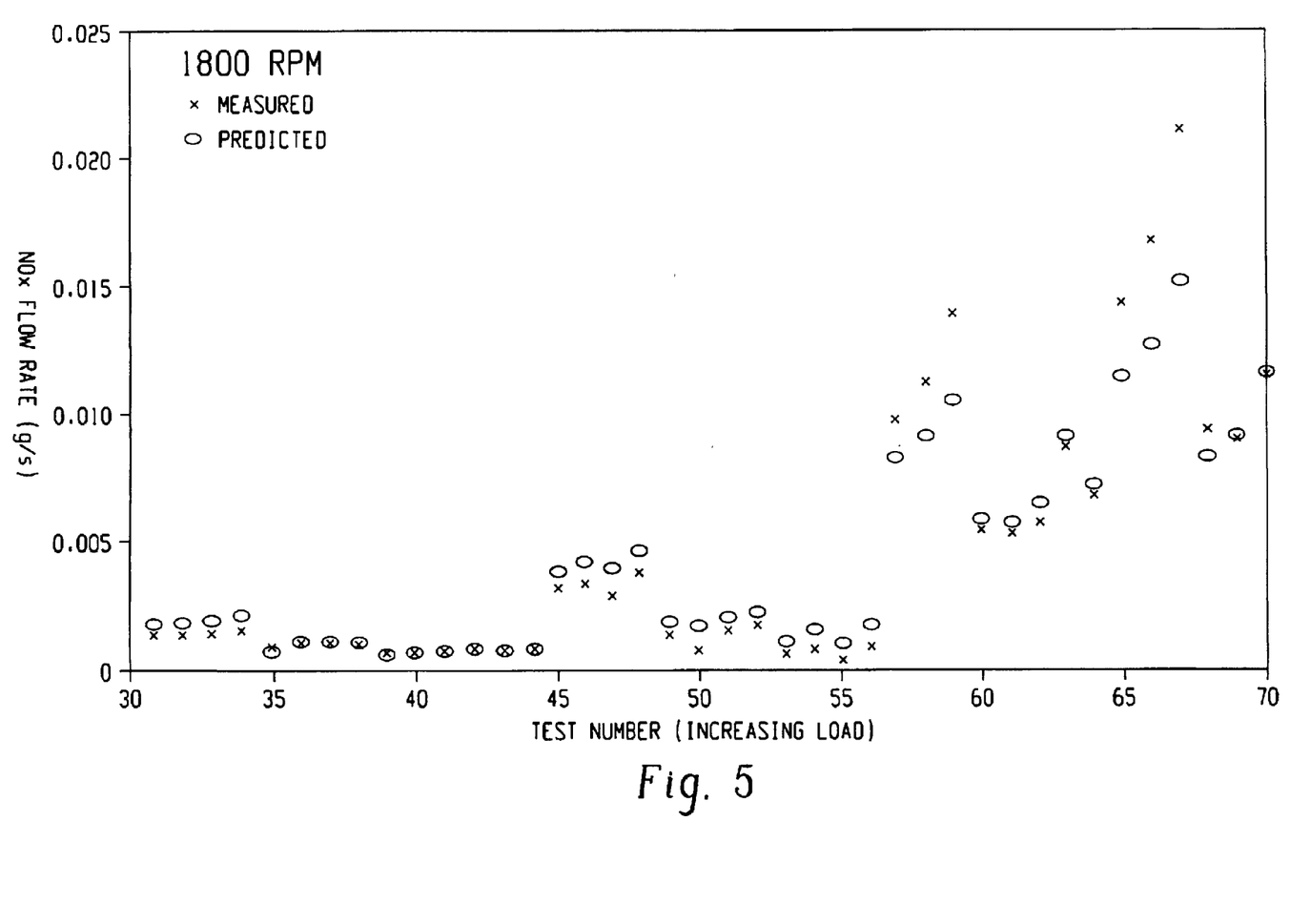
FIG. 5 is a graphical illustration of model predictions and measurement of NOx flow rate as a function of test number for a 1.3 liter engine running at 1,800 rpm.
Figure 6:
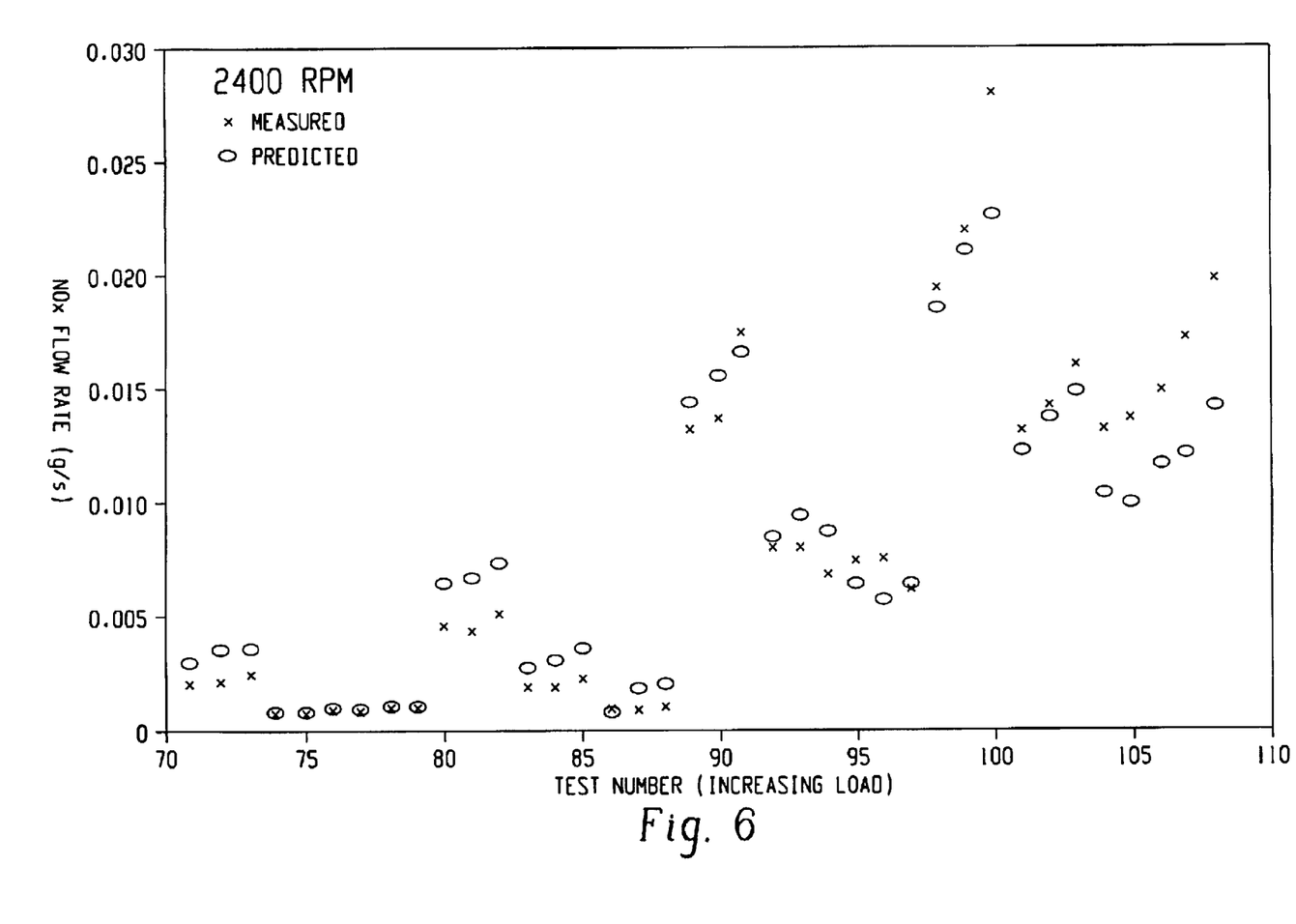
FIG. 6 is a graphical illustration of model predictions and measurement of NOx flow rate as a function of test number for a 1.3 liter engine running at 2,400 rpm.
Figure 7:
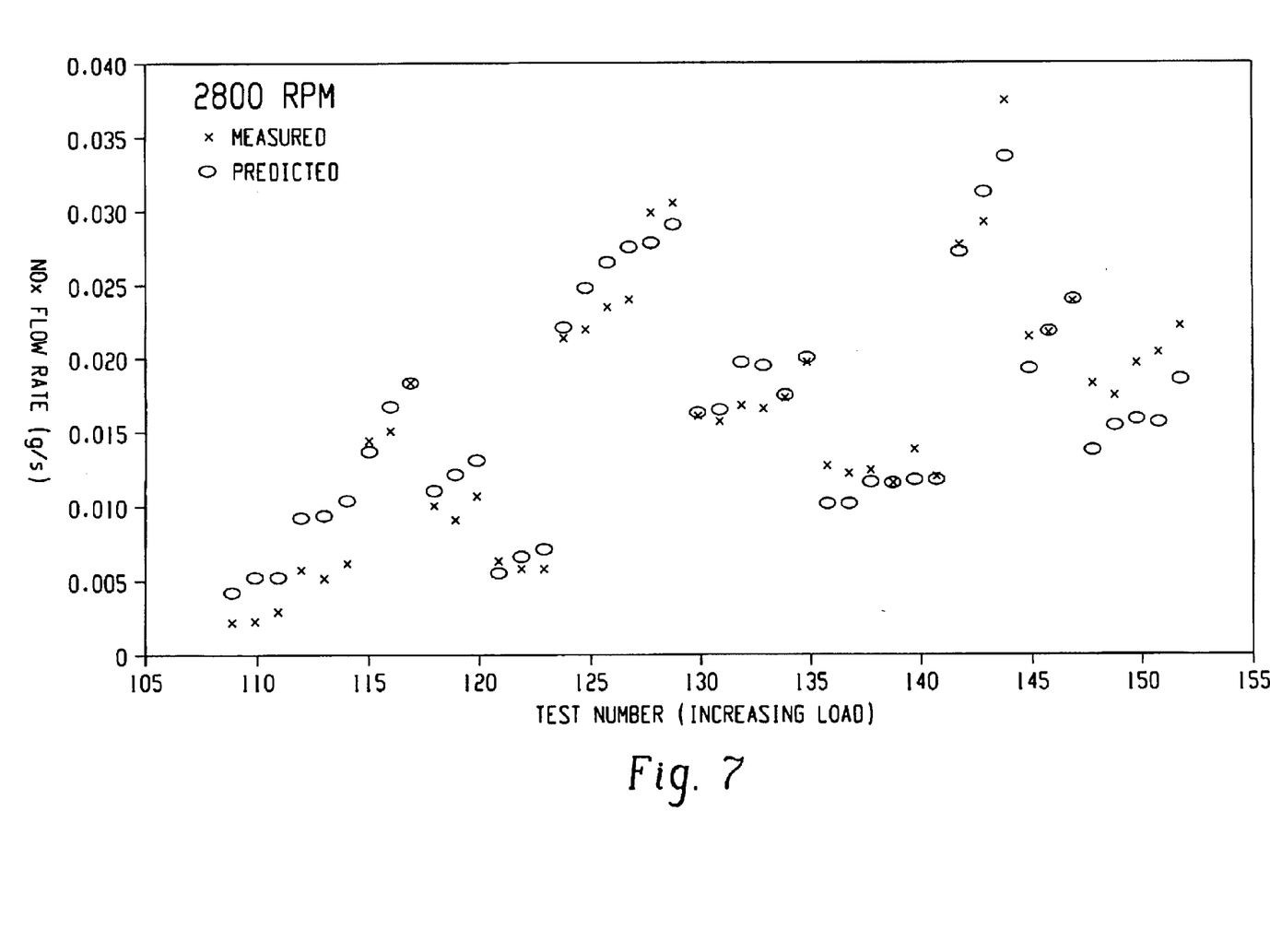
FIG. 7 is a graphical illustration of model predictions and measurement of NOx flow rate as a function of test number for a 1.3 liter engine running at 2,800 rpm.
Figure 8:
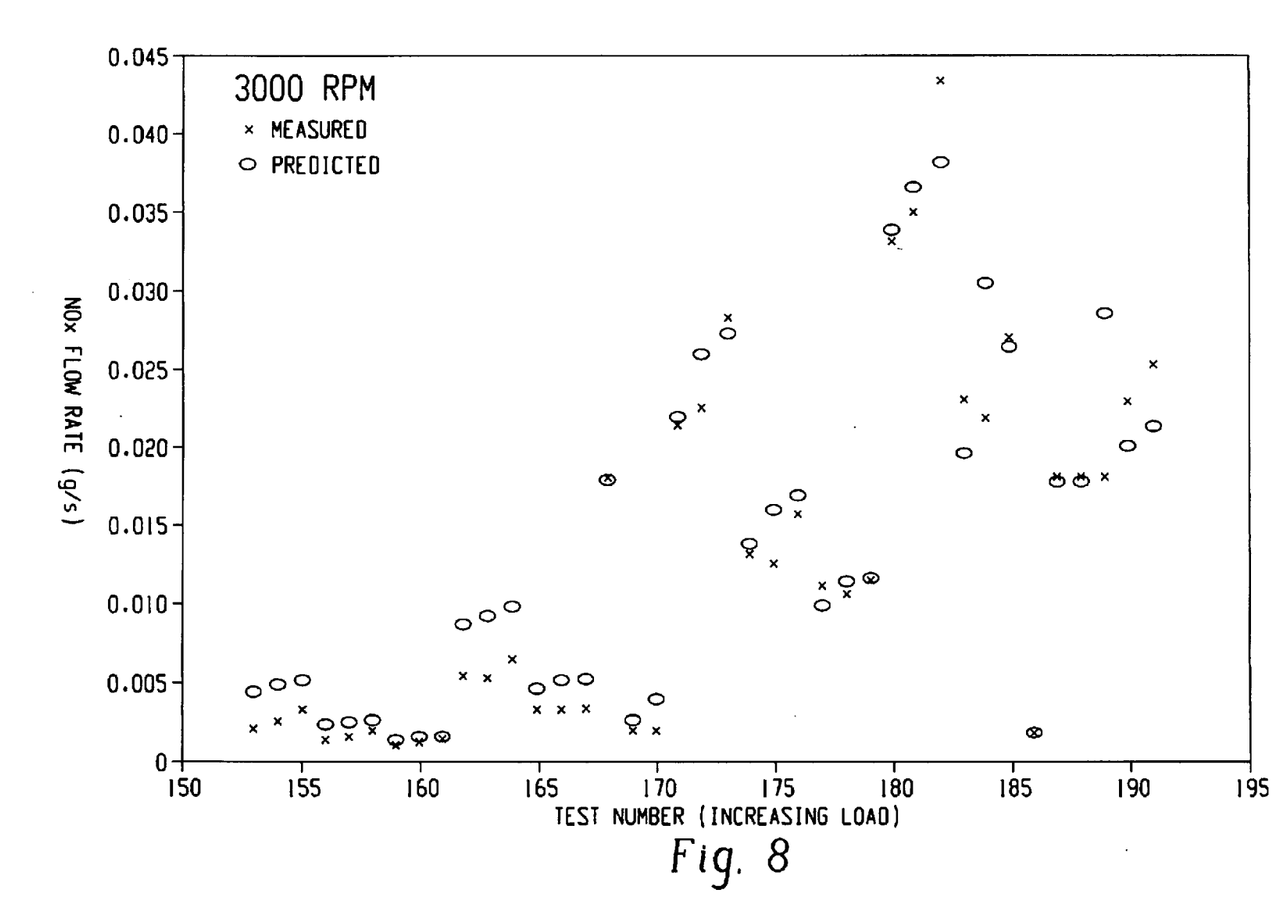
FIG. 8 is a graphical illustration of model predictions and measurement of NOx flow rate as a function of test number for a 1.3 liter engine running at 3,000 rpm.

FIG. 3 shows implementation of the in-cylinder model in a Simulink function block format. The inputs for estimating NOx output include (1) trapped air, fuel and EGR masses for each cycle, (2) exhaust gas concentration, i.e., a total mass of species generated within a combustion zone as a fraction of total in-cylinder mass determined from a ratio of the combustion zone mass to the in-cylinder mass, (3) fuel fraction burned up to maximum temperature time, and (4) a chemical equilibrium calculation value based upon the $T_{burn}$ correlation, which is dependent upon the trapped air mass, the cylinder pressure at maximum temperature, and the cylinder pressure at top dead center.

Figure 9:
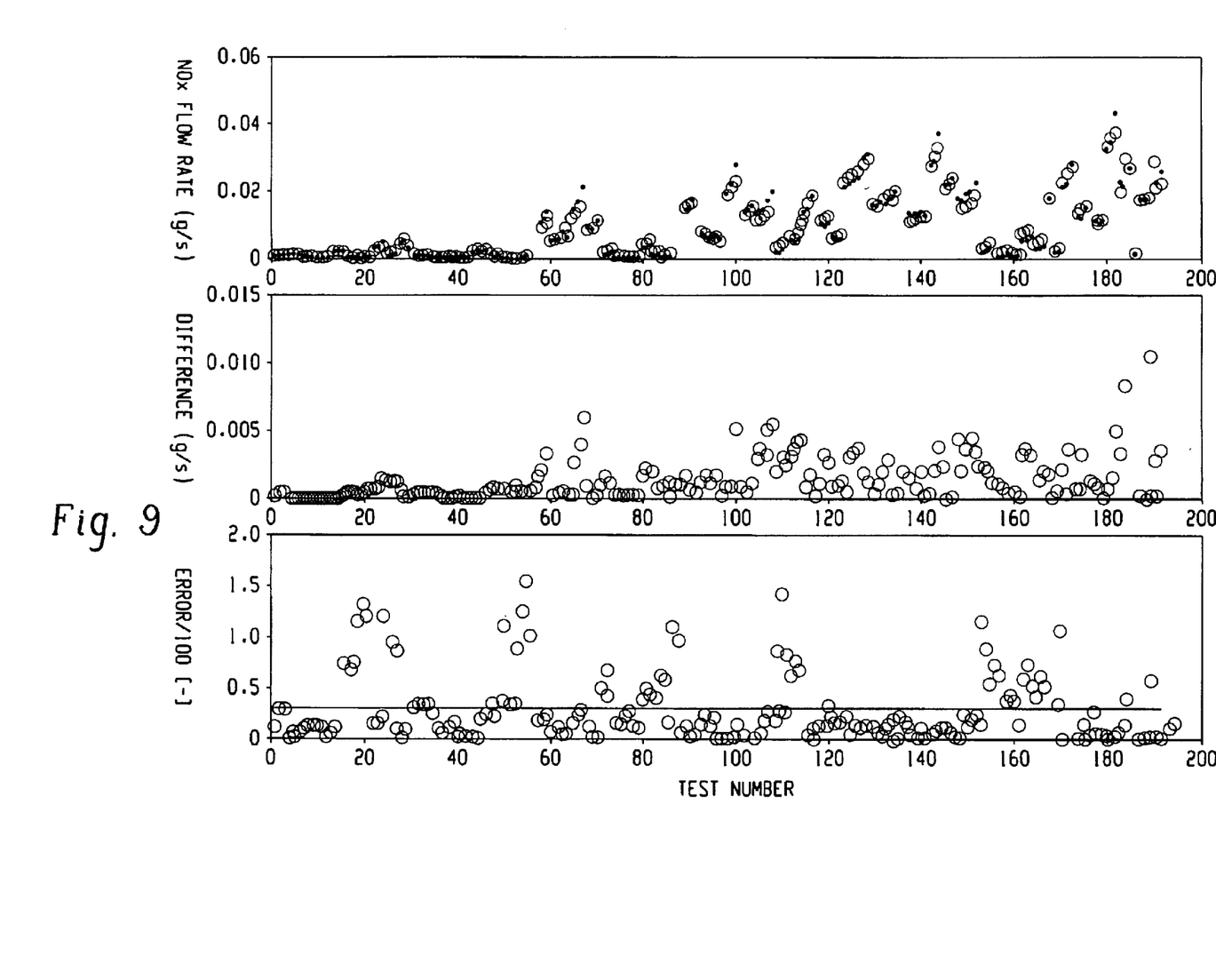
FIG. 9 is graphical illustration showing error comparisons for the data illustrated in FIGS. 4–8.

The results comparing the estimated NOx output values versus the actual measurements are graphically shown in FIGS. 4–8. FIG. 9 displays the full test matrix used and presents the overall correlation of the model with the actual measurements. FIG. 9 also shows the residuals and the error percentage. The results clearly indicate the robustness of the estimation model. The predicted NOx values closely overlapped the actual measurements under most conditions. However, under some operating conditions it is apparent that the error percentages are relatively high compared to the results obtained under most conditions. While not wanting to be bound by theory, a possible reason for these relatively high errors is either: a) a result of low measured values, wherein small absolute error values may possibly have resulted in high error percentages such as when observing the residuals for these points, or b) the combustion process resulted in significant smoke numbers, which suggests that the model might not be as accurate at high equivalence ratios compared to lean combustion conditions.

Advantageously, the in-cylinder model for providing real-time estimates of NOx production during a combustion cycle offers at least the following advantages:

1. Real-time "transient" model, although it is based on steady state data but it is a function of the in-cylinder cycle-by-cycle parameters;
2. Runs once per cycle, which minimizes the computational expense;
3. Easy integration with combustion models that are used to estimate the in-cylinder combustion characteristics;
4. Reduced effective parameters that affect the estimation of NOx production from diesel combustion;
5. Use of the model can potentially eliminate the use of engine-out NOx sensors that may eventually be required for production diesel engines in order to meet future emission standards;
6. Calibration of the engine is not required to employ the model; and
7. The look-up table is based on chemical equilibrium calculations, and as such, the table values are static and do not change.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A process for providing a real-time estimation of in-cylinder NOx production rates during a combustion process in an internal combustion engine, the process comprising:
    receiving a plurality of input values from a combustion chamber of a cylinder, wherein the input values consist essentially of a mass amount of trapped air in the combustion chamber, a mass amount of trapped fuel in the combustion chamber, a total mass of species generated within a combustion zone as a fraction of total in-cylinder mass, and a correlation value from a lookup table derived from an average NOx temperature of the combustion zone; and
    calculating an output signal from the plurality of input values, wherein the output signal produces a real-time estimate of the NOx production rate from the cylinder.

2. The process according to claim 1, wherein the average NOx temperature value is determined from a trapped air mass value, a cylinder pressure at top dead center, and a cylinder pressure at maximum temperature.

3. The process according to claim 1, wherein the average NOx temperature value is calculated in accordance with the following mathematical relationship:

$$T_{burn} = a\left(1 + \frac{m_{air}}{m_{stp}}\right)^b \left[1 + \frac{p_{T\,max}}{p_{TDC}}\right]^c,$$

wherein $T_{burn}$ is the average NOx temperature, $m_{air}$ is a trapped air mass value, $m_{stp}$ is a trapped mass value at standard temperature and pressure with a volumetric efficiency of 1, $P_{Tmax}$ is a cylinder pressure at maximum temperature, $P_{TDC}$ is a cylinder pressure at top dead center, and a, b, and c are constants.

4. The process according to claim 1, wherein the average NOx temperature is determined at a peak in-cylinder average temperature condition.

5. The process according to claim 1, wherein the combustion zone comprises reacting burned fuel at a peak temperature with a stoichiometric amount of air and a recirculated exhaust gas.

6. The process according to claim 1, wherein the correlation value comprises a chemical equilibrium calculation for NOx species produced in the combustion zone.

7. The process according to claim 6, wherein the chemical equilibrium calculation comprises determining a mole fraction of species produced in the combustion zone at the average temperature value by minimizing a total Gibbs free energy for all species.

8. A process for providing a real-time estimation of in-cylinder NOx production rates during a combustion process in an internal combustion engine comprising:
    calculating an average NOx producing temperature value in a combustion zone of a cylinder combustion chamber;
    correlating the average NOx producing temperature value to a correlation value in a look-up table; and
    estimating the in-cylinder NOx production rate from a calculation including the correlation value, an amount of trapped air in the combustion chamber, an amount of trapped unburned fuel in the combustion chamber, and a total mass of species generated within a combustion zone as a fraction of total in-cylinder mass.

9. The process according to claim 8, wherein the average temperature value is determined from a mathematical relationship comprising:

$$T_{burn} = a\left(1 + \frac{m_{air}}{m_{stp}}\right)^b \left[1 + \frac{p_{T\,max}}{p_{TDC}}\right]^c,$$

wherein $T_{burn}$ is the average temperature value, $m_{air}$ is a trapped air mass value, $m_{stp}$ is a trapped mass value at standard temperature and pressure with a volumetric efficiency of 1, $P_{Tmax}$ is a cylinder pressure at maximum temperature, $P_{TDC}$ is a cylinder pressure at top dead center, and a, b, and c are constants.

10. The process according to claim 8, wherein the correlation value comprises a chemical equilibrium calculation for the NOx species.

11. The process according to claim 8, is dependent on in from a mass air flow value, a cylinder pressure at top dead center, and a cylinder pressure at maximum temperature within a combustion zone.

12. The process according to claim 11, wherein the chemical equilibrium calculation comprises determining a mole fraction of species produced in the combustion zone at the average temperature value by minimizing a total Gibbs free energy for all species.

* * * * *